(12) United States Patent
Raveglia et al.

(10) Patent No.: US 7,531,692 B2
(45) Date of Patent: May 12, 2009

(54) DERIVATIVES OF 1-PHENYLALKANECARBOXYLIC ACIDS FOR THE TREATMENT OF NEURODEGENERATIVE DISEASES

(75) Inventors: Luca Raveglia, Parma (IT); Ilaria Peretto, Parma (IT); Stefano Radaelli, Parma (IT); Bruno Pietro Imbimbo, Parma (IT); Andrea Rizzi, Parma (IT); Gino Villetti, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 11/572,974

(22) PCT Filed: Jul. 26, 2005

(86) PCT No.: PCT/IB2005/002189

§ 371 (c)(1),
(2), (4) Date: Oct. 12, 2007

(87) PCT Pub. No.: WO2006/016219

PCT Pub. Date: Feb. 16, 2006

(65) Prior Publication Data

US 2008/0096968 A1    Apr. 24, 2008

(30) Foreign Application Priority Data

Aug. 3, 2004  (EP)  ................... 04425604

(51) Int. Cl.
*C07C 233/05* (2006.01)
*A61K 31/16* (2006.01)

(52) U.S. Cl. ...................... 564/155; 514/616

(58) Field of Classification Search ............... 564/155; 514/616

See application file for complete search history.

(56) References Cited

U.S. PATENT DOCUMENTS

| 6,114,391 | A | 9/2000 | Chiesi et al. |
|---|---|---|---|
| 6,117,901 | A | 9/2000 | Wu et al. |
| 6,191,166 | B1 | 2/2001 | Audia et al. |
| 6,476,263 | B1 | 11/2002 | Wu et al. |
| 2002/0052322 | A1 | 5/2002 | Audia et al. |
| 2007/0060752 | A1 | 3/2007 | Raveglia et al. |

FOREIGN PATENT DOCUMENTS

| WO | 99 41224 | 8/1999 |
|---|---|---|
| WO | 2004 009565 | 1/2004 |

OTHER PUBLICATIONS

Tomiyama et al, Oya Yakuri, 1980, 19(6), 895-900.*
Turbanti et al, Farmaco, Edizione Scientifica, 1960, 15, 406-13(Abstract only).*
L. Turbanti, G. F. Di Paco, "Acidi α-Difenililetilacetamino-β-Arilacrilici A Prusunta Azione Coleretica E Ipocolesteroiemica", Il Farmaco-ED. Sc., vol. 15, No. 6, pp. 406-413, 1960.
U.S. Appl. No. 11/572,974, filed Jan. 30, 2007, Raveglia et al.

* cited by examiner

*Primary Examiner*—Shailendra Kumar
(74) *Attorney, Agent, or Firm*—Oblon, Spivak, McClelland, Maier & Neustadt, P.C.

(57) ABSTRACT

The present invention concerns novel derivatives of 1-phenylalkanecarboxylic acids, pharmaceutical compositions thereof, a process for their preparation and their use for the treatment and/or prevention of neurodegenerative diseases such as Alzheimer's disease.

21 Claims, No Drawings ical point of view, by atrophy of the cerebral cortex
DERIVATIVES OF 1-PHENYLALKANECARBOXYLIC ACIDS FOR THE TREATMENT OF NEURODEGENERATIVE DISEASES

CROSS REFERENCES TO RELATED APPLICATIONS

This application is a 371 of International Patent Application No. PCT/IB05/02189, filed on Jul. 26, 2005, and claims priority to European Patent Application No. 04425604.8, filed on Aug. 3, 2004.

The present invention concerns novel derivatives of 1-phenylalkanecarboxylic acids, pharmaceutical compositions thereof, a process for their preparation and their use for the treatment of neurodegenerative diseases, in particular Alzheimer's disease.

INTRODUCTION

Alzheimer's disease is a neurodegenerative disorder of the Central Nervous System (C.N.S.) characterized, from the anathomical point of view, by atrophy of the cerebral cortex and by a massive loss of cortical neurons and cholinergic projections of the nuclei basalis towards the cortex. From the histopathologic point of view a diffuse presence of extracellular and perivascular neuritic plaques and intracellular neurofibrillary tangles in the cerebral parenchyma of the patients is observed.

Neuritic plaques are mainly composed of aggregates of a peptide with 39-43 amino acid residues known as β-amyloid (βA), and, depending on the numbers of amino acids, $A\beta_{39}$, $A\beta_{40}$, $A\beta_{42}$ and $A\beta_{43}$.

In addition to these histopathologic lesions, there is lack in some neurotransmitters, particularly acetylcholine, serotonin, noradrenalin, dopamine, glutamate and substance P. The pharmacological approaches aimed at increasing acetylcholine cerebral levels, mainly through acetylcholine-esterase inhibitors, attained poor results from the clinical standpoint, or anyhow results which cannot significantly prevent the progress of the disease. For this reason, in recent years the mechanisms of formation of the main pathologic lesions in the brain of the patients have been investigated, namely both neuritic plaques and neurofibrillary tangles, and more effective therapeutical approaches have been sought.

PRIOR ART

Epidemiological studies evidenced that chronic administration of non steroid anti-inflammatory drugs (NSAIDs) significantly decreases the risk of onset of Alzheimer's disease in the population regularly taking these drugs. The mechanism underlying such NSAIDs preventive action has not been fully elucidated yet, but in the earlier hypothesis, it was connected with their inherent anti-inflammatory activity, i.e. with their ability of inhibiting the cyclooxygenase (COX) enzyme.

In WO 99/41224 novel biaryl-acetic acid derivatives with anti-inflammatory activity as cyclooxygenase-2 inhibitors, useful for the treatment of a number of diseases, including Alzheimer's disease, are claimed.

More recently, a novel pharmacological action of some non steroid anti-inflammatory drugs (NSAIDs) has been described: indomethacin, sulindac, ibuprofen and flurbiprofen can selectively reduce the production of the most neurotoxic isoform of β-amyloid peptide in cell cultures, namely the form containing 42 amino acids ($A\beta_{42}$), thus favoring the release of a less harmful isoform, $A\beta_{38}$ (Weggen et al., Nature 2001; 414 (6860): 212-6). However, the inhibition of the production of $A\beta_{42}$, which can be ascribed to the interaction of these drugs with γ-secretase enzyme (a macromolecular/multiprotein complex with aspartyl-protease activity) has been observed in vitro at very high concentrations. Plasma and cerebral levels corresponding to the dosages used in the in vitro experimentation could significantly increase in treated patients the risk of side effects typical of COX inhibitors, such as gastrointestinal bleeding and perforating ulcers.

WO 01/78721 claims a method of preventing, delaying or reversing the progression of Alzheimer's disease by administering an $A\beta_{42}$ lowering agent, under conditions in which levels of $A\beta_{38}$ are increased and levels of $A\beta_{42}$ are left unchanged. Furthermore, methods and materials for identifying and developing $A\beta_{42}$ lowering agents and methods for identifying agents that increase the risk of developing, or hasten progression of Alzheimer's disease, are disclosed. The examples concern indomethacin and flufenamic acid derivatives, but no examples concerning flurbiprofen derivatives are reported.

Jantzen et al, *J Neurosci* 2002; 22: 2246-2254, described a flurbiprofen derivative capable of releasing nitric oxide. The paper generically states that flurbiprofen derivatives are apparently more efficacious than other NSAIDs in clearing β-amyloid deposits, but no mention concerning an $A\beta_{42}$ lowering selective activity is made.

In the co-pending International application No. PCT/EP2004/001596 the applicant claims 1-phenylalkanecarboxylic acids and their functional derivatives such as esters, amides, sulfonamides, and bioisosters as compounds provided with a more selective and more potent inhibitory activity on the peptide $A\beta_{42}$ than that on the cyclooxygenase enzymes.

On the other hand, drugs aimed at the treatment of C.N.S. diseases such as Alzheimer's disease, in order to efficaciously exercise their therapeutic activity, need to cross the blood-brain barrier. The passage and the distribution in the C.N.S. of polar drugs such the carboxylic acids and their derivatives are strongly limited by the presence of said barrier.

Therefore it would be highly advantageous to provide carrier molecules to link said 1-phenylalkanecarboxylic acids in such a way to obtain novel compounds acting as pro-drugs able of crossing more efficaciously the blood-brain barrier and then, releasing in situ the active moiety of the molecule in order to allow its distribution in the brain.

SUMMARY OF THE INVENTION

The present invention concerns novel derivatives of 1-phenylalkanecarboxylic acids, pharmaceutical compositions thereof, a process for their preparation and their use for the prevention or therapeutical treatment of neurodegenerative diseases connected with an increased production of the neurotoxic peptide $A\beta_{42}$, in particular Alzheimer's disease.

In particular the invention concerns derivatives of 1-phenylalkanecarboxylic acids wherein the carboxylic group is linked to a residue allowing the passage of the blood-brain barrier and the distribution of the active moiety in the brain.

In an embodiment of the invention, said residue is represented by the amide of an alpha-amino acid and preferably is glycinamide.

DETAILED DESCRIPTION OF THE INVENTION

The present invention is directed to compounds of general formula (I):

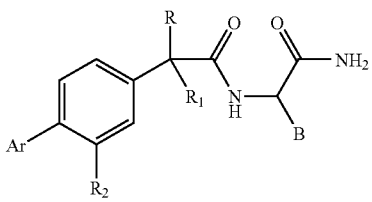

wherein:

B is H or the side chain of an alpha-amino acid;

R and $R_1$ are the same and are a linear or branched $C_1$-$C_4$ alkyl;

or they form a 3 to 6 carbon atoms ring with the carbon atom to which they are linked;

$R_2$ is H, $CF_3$, $OCF_3$ or a halogen selected from the group of F, Cl, Br, I, preferably fluorine.

Ar is phenyl substituted with one or more groups $R_3$ wherein $R_3$ represents:

halogen as previously defined; $CF_3$; $C_3$-$C_8$ cycloalkyl optionally substituted with one or more $C_1$-$C_4$ alkyl and/or oxo groups; $CH=CH_2$; $NO_2$; $CH_2OH$; CN; methylenedioxy; ethylenedioxy;

phenyl optionally substituted with one or more of the following groups: halogen as previously defined; $CF_3$, $OCF_3$, OH; linear or branched $C_1$-$C_4$ alkyl; a saturated heterocycle with at least 4 carbon atoms and at least 1 heteroatom; $C_3$-$C_8$ cycloalkyl optionally substituted with one or more linear or branched $C_1$-$C_4$ alkyl groups, $CF_3$ and/or OH;

$OR_4$ or $NHCOR_4$ wherein $R_4$ is $CF_3$, linear or branched $C_2$-$C_6$ alkenyl or alkynyl; benzyl; phenyl optionally substituted with one or more of the following groups: halogen as previously defined, $CF_3$, $OCF_3$, OH, linear or branched $C_1$-$C_4$ alkyl; a saturated heterocycle with at least 4 carbon atoms and at least 1 heteroatom; $C_3$-$C_8$ cycloalkyl optionally substituted with one or more linear or branched $C_1$-$C_4$ alkyl groups, $CF_3$ and/or OH;

$SR_5$, $SO_2R_5$ or $COR_5$ wherein $R_5$ is linear or branched $C_1$-$C_6$ alkyl;

or Ar is a heterocycle selected from the group consisting of pyrrole, pyrazole, furan, thiophene, indole, isoindole, benzofuran, benzothiophene, imidazole, oxazole, isoxazole, thiazole, benzoimidazole, benzoxazole, benzothiazole, pyrimidine, pyrazine, quinoline, isoquinoline, quinazoline, quinoxaline, dibenzofuran, dibenzothiophene, thianthrene, carbazole, pyridazine, cinnoline, phthalazine, 1,5-naphthiridine, 1,3-dioxole, 1,3-benzodioxole, said heterocycle being optionally substituted with one or more groups $R_3$ as defined above.

Amides of an alpha-amino acid representative of the invention are preferably selected from the group of glycinamide, alanylamide, serinamide, and valinamide, even more preferably in the levo form.

The preferred amide is glycinamide ($H_2NCH_2CONH_2$).

A first group of preferred compounds is that in which:

B is H;

R and $R_1$ form a 3 carbon atoms ring;

$R_2$ is fluorine;

Ar is phenyl as defined above.

A second group of preferred compounds is that in which:

B is H;

R and $R_1$ are both methyl;

$R_2$ is fluorine;

Ar is phenyl as defined above.

A third group of preferred compounds is that in which:

B is H;

R and $R_1$ form a 3 carbon atoms ring;

$R_2$ is fluorine;

Ar is a heterocycle as defined above.

A fourth group of preferred compounds is that in which:

B is H;

R and $R_1$ are both methyl;

$R_2$ is fluorine;

Ar is a heterocycle as defined above.

The invention also includes the enantiomers, metal and organic salts and other esters pharmaceutically acceptable.

A further object of the present invention is the use of the aforementioned compounds for the therapeutical treatment and/or prevention of neurodegenerative diseases connected with an increased production of the neurotoxic peptide $A\beta_{42}$, such as Alzheimer's disease.

Still a further object of the invention are solid or liquid pharmaceutical compositions, preferably for the oral use, comprising at least one compound of formula (I) in admixture with pharmaceutically acceptable excipients and/or vehicles, for example those described in Remington's Pharmaceutical Sciences Handbook, XVII Ed., Mack Pub., N.Y., U.S.A.

The compounds of general formula (I) can be prepared according to methods known literature by conversion of an acid of formula (II)

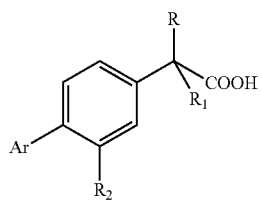

in which R, $R_1$, $R_2$, and Ar are as defined above, into the corresponding acyl chloride, followed by reaction with the amide of the suitable alpha-amino acid.

Alternatively, said compounds can be prepared by direct reaction of the acid of formula (II) with the amide of the suitable alpha-amino acid in the presence of coupling agents such as dycyclohexylcarbodiimide (DCC), polymer supported-DCC, or N,N'carbonyldiimidazole or treating a corresponding ester with the compound formed in situ by reacting trimethylaluminium and the amide of a suitable alpha-amino acid.

The acids of formula (II) can be prepared as described in the co-pending International application No. PCT/EP2004/001596.

EXAMPLES

The following Example illustrates the invention in a more detail.

Preparation of the glycinamide of the 1-[2-fluoro-4'-[[4-(trifluoromethyl)-cyclohexyl]oxy]-1,1'-biphenyl-4-yl]-cyclopropanecarboxylic acid Preparation of the 1-(2-fluoro-4'-hydroxy-biphenyl-4-yl)-cyclopropanecarboxylic acid To a solution of $K_2CO_3$ (447 mg, 3.2 mmoles) in dioxane (30 ml) and water (3 ml), 250 mg of 1-(4-bromo-3-fluoro-phenyl)-cyclopropanecarboxylic acid (1.0 mmole) and 265 mg of hydroxyphenylboronic acid (1.9 mmoles) are added under stirring. Under nitrogen atmosphere, 39 mg of [1,1'-bis (diphenylphosphino)ferrocene]dichloropalladium (PdCl$_2$-DPPF) are added. The resulting mixture is heated at 65° C. for one hour, then the reaction is quenched by adding a 10% w/v HCl solution.

Extractions with ethyl acetate, washings with water and brine and evaporation afford the crude product, which is crystallized from ethyl acetate/hexane, to give the 1-(2-fluoro-4'-hydroxy-biphenyl-4-yl)-cyclopropanecarboxylic acid. Yield: 85%.

Preparation of the 1-[2-fluoro-4'-(4-trifluoromethyl-cyclohexyloxy)-biphenyl-4-yl]-cyclopropanecarboxylic acid Diethyl azodicarboxylate (370 μL, 2.4 mmoles) is added to a solution of 200 mg of 1-(2-fluoro-4'-hydroxy-biphenyl-4-yl)-cyclopropanecarboxylic acid (0.8 mmoles), triphenyl phosphine (623 mg, 2.4 mmoles) and 4-trifluoromethyl cyclohexanol (400 mg, 2.4 mmoles) in dry THF (3 mL) at 0° C. under nitrogen atmosphere. The resulting clear orange solution is left under stirring overnight, then quenched with water and extracted with ethyl acetate. The organic phase is washed with 10% w/v HCl solution, dried on Na$_2$SO$_4$ and evaporated. Purification by chromatography on silica gel by eluting with methylene chloride:methanol 98:2 v/v furnishes 1-[2-fluoro-4'-(4-trifluoromethyl-cyclohexyloxy)-biphenyl-4-yl]-cyclopropanecarboxylic acid as a white solid.
Yield: 26%.
HPLC purity (254 nm): 98%

Preparation of the glycinamide of the 1-[2-fluoro-4'-(4-trifluoromethyl-cyclohexyloxy)-biphenyl-4-yl]-cyclopropanecarboxylic acid Oxalyl chloride (530 μL, 6.0 mmoles) is added dropwise to a solution of 1-[2-fluoro-4'-(4-trifluoromethyl-cyclohexyloxy)-biphenyl-4-yl]-cyclopropane carboxylic acid (480 mg, 1.0 mmoles) in 5 ml of methylene chloride, under nitrogen. The resulting solution is stirred at room temperature for 2 hours, then evaporated to dryness and redissolved in methylene chloride. A suspension of glycinamide hydrochloride (133 mg. 1.3 mmoles) and triethylamine (3 ml) in 5 ml of methylene chloride is added to the solution and the resulting mixture is stirred for 2 hours at room temperature. After addition of water, the organic phase is washed with a 2N K$_2$CO$_3$ solution and brine, dried on Na$_2$SO$_4$ and evaporated. The solid obtained is purified by chromatography. After recrystallization from ethyl acetate/petroleum ether a white solid is obtained.
HPLC purity (254 nm): 98%.
MS (ESI$^+$): 479.2 (MH$^+$).
$^1$H NMR(CDCl$_3$): 7.47 (dd, 2H); 7.43 (dd, 1H); 7.25 (dd, 1H); 7.19 (dd, 1H); 6.97 (dd, 2H); 6.05 (t, 1H); 5.94 (s, 1H); 5.34 (s, 1H); 4.23 (m, 1H); 3.88 (d, 2H); 2.35-2.25 (m, 2H); 2.15-2.01 (m, 3H); 1.64 (m, 2H); 1.48 (dd, 4H); 1.14 (m, 2H).
Legend: dd=doublet of doublets; t=triplet; d=doublet; s=singlet; m=multiplet.

The invention claimed is:
1. A compound of formula (I):

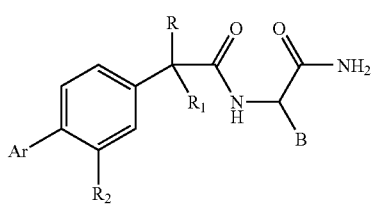

(I)

wherein:
B is H or the side chain of an alpha-amino acid;
R and R$_1$ are the same and are linear or branched C$_1$-C$_4$ alkyl;
or together with the carbon atom to which they are linked form a ring containing 3 to 6 carbon atoms;
R$_2$ is H, CF$_3$, OCF$_3$ or a halogen selected from the group consisting of F, Cl, Br, and I; and
Ar is phenyl substituted with one or more groups R$_3$, wherein R$_3$ represents:
halogen selected from the group consisting of F, Cl, Br, and I; CF$_3$; C$_3$-C$_8$ cycloalkyl optionally substituted with one or more C$_1$-C$_4$ alkyl and/or oxo groups; CH=CH$_2$; NO$_2$; CH$_2$OH; CN; methylenedioxy; ethylenedioxy; phenyl optionally substituted with one or more of the following groups: halogen selected from the group consisting of F, Cl, Br, and I; CF$_3$; OCF$_3$; OH; linear or branched C$_1$-C$_4$ alkyl; a saturated heterocycle with at least 4 carbon atoms and at least 1 heteroatom; and C$_3$-C$_8$ cycloalkyl optionally substituted with one or more linear or branched C$_1$-C$_4$ alkyl groups, CF$_3$ and/or OH; OR$_4$ or NHCOR$_4$ wherein R$_4$ is CF$_3$, linear or branched C$_2$-C$_6$ alkenyl or alkynyl; benzyl; phenyl optionally substituted with one or more of the following groups: halogen as previously defined, CF$_3$, OCF$_3$, OH, linear or branched C$_1$-C$_4$ alkyl; a saturated heterocycle with at least 4 carbon atoms and at least 1 heteroatom; C$_3$-C$_8$ cycloalkyl optionally substituted with one or more linear or branched C$_1$-C$_4$ alkyl groups, CF$_3$ and/or OH; and SR$_5$, SO$_2$R$_5$ or COR$_5$ wherein R$_5$ is linear or branched C$_1$-C$_6$ alkyl; or
Ar is a heterocycle selected from the group consisting of pyrrole, pyrazole, furan, thiophene, indole, isoindole, benzofuran, benzothiophene, imidazole, oxazole, isoxazole, thiazole, benzoimidazole, benzoxazole, benzothiazole, pyrimidine, pyrazine, quinoline, isoquinoline, quinazoline, quinoxaline, dibenzofuran, dibenzothiophene, thianthrene, carbazole, pyridazine, cinnoline, phthalazine, 1,5-naphthiridine, 1,3-dioxole, and 1,3-benzodioxole, said heterocycle being optionally substituted with one or more groups R$_3$ as defined above;
or a pharmaceutically acceptable salt or ester thereof.
2. The compound or pharmaceutically acceptable salt or ester thereof as claimed in claim 1, wherein B is H.
3. The compound or pharmaceutically acceptable salt or ester thereof as claimed in claim 1, wherein B is H; R and R$_1$ together with the carbon atom to which they are linked form a ring containing 3 carbon atoms; R$_2$ is fluorine; and Ar is substituted phenyl.
4. The compound or pharmaceutically acceptable salt or ester thereof as claimed in claim 1, wherein B is H; R and R$_1$ are both CH$_3$; R$_2$ is fluorine; and Ar is substituted phenyl.
5. The compound or pharmaceutically acceptable salt or ester thereof as claimed in claim 1, wherein B is H; R and R$_1$ together with the carbon atom to which they are linked form a ring containing 3 carbon atoms; R$_2$ is fluorine; and Ar is a substituted or unsubstituted heterocycle.
6. The compound or pharmaceutically acceptable salt or ester thereof as claimed in claim 1, wherein B is H; R and R$_1$ are both CH$_3$; R$_2$ is fluorine; and Ar is a substituted or unsubstituted heterocycle.
7. A compound or pharmaceutically acceptable salt thereof as claimed in claim 1.

8. A pharmaceutical composition, comprising a compound of formula (I) or pharmaceutically acceptable salt or ester thereof as claimed in claim 1 in admixture with a pharmaceutically acceptable carrier.

9. The pharmaceutical composition as claimed in claim 8, which is in a form suitable for oral administration.

10. The compound or pharmaceutically acceptable salt or ester thereof according to claim 1, wherein $R_2$ is F.

11. A pharmaceutical composition, comprising a compound of formula (I) or pharmaceutically acceptable salt or ester thereof as claimed in claim 2 in admixture with a pharmaceutically acceptable carrier.

12. A pharmaceutical composition, comprising a compound of formula (I) or pharmaceutically acceptable salt or ester thereof as claimed in claim 3 in admixture with a pharmaceutically acceptable carrier.

13. A pharmaceutical composition, comprising a compound of formula (I) or pharmaceutically acceptable salt or ester thereof as claimed in claim 4 in admixture with a pharmaceutically acceptable carrier.

14. A pharmaceutical composition, comprising a compound of formula (I) or pharmaceutically acceptable salt or ester thereof as claimed in claim 5 in admixture with a pharmaceutically acceptable carrier.

15. A pharmaceutical composition, comprising a compound of formula (I) or pharmaceutically acceptable salt or ester thereof as claimed in claim 6 in admixture with a pharmaceutically acceptable carrier.

16. A pharmaceutical composition, comprising a compound of formula (I) or pharmaceutically acceptable salt thereof as claimed in claim 1 in admixture with a pharmaceutically acceptable carrier.

17. A pharmaceutical composition, comprising a compound of formula (I) or pharmaceutically acceptable salt thereof as claimed in claim 2 in admixture with a pharmaceutically acceptable carrier.

18. A pharmaceutical composition, comprising a compound of formula (I) or pharmaceutically acceptable salt thereof as claimed in claim 3 in admixture with a pharmaceutically acceptable carrier.

19. A pharmaceutical composition, comprising a compound of formula (I) or pharmaceutically acceptable salt thereof as claimed in claim 4 in admixture with a pharmaceutically acceptable carrier.

20. A pharmaceutical composition, comprising a compound of formula (I) or pharmaceutically acceptable salt thereof as claimed in claim 5 in admixture with a pharmaceutically acceptable carrier.

21. A pharmaceutical composition, comprising a compound of formula (I) or pharmaceutically acceptable salt thereof as claimed in claim 6 in admixture with a pharmaceutically acceptable carrier.

* * * * *